United States Patent [19]
Hempel, deceased

[11] Patent Number: 5,332,847
[45] Date of Patent: Jul. 26, 1994

[54] PROCESS FOR THE PREPARATION OF 21-BROMO-4-PREGNENE-3,20-DIONE DERIVATIVES

[75] Inventor: Gerhard Hempel, deceased, late of Werne, Fed. Rep. of Germany, by Gabriele M. K. Hempel, heiress

[73] Assignee: Schering Aktiengesellschaft, Berlin und Bergkamen, Fed. Rep. of Germany

[21] Appl. No.: 663,913

[22] PCT Filed: May 7, 1990

[86] PCT No.: PCT/DE90/00329

§ 371 Date: Mar. 11, 1991

§ 102(e) Date: Mar. 11, 1991

[87] PCT Pub. No.: WO90/13558

PCT Pub. Date: Nov. 15, 1990

[30] Foreign Application Priority Data

May 12, 1989 [DE] Fed. Rep. of Germany ....... 3915951

[51] Int. Cl.$^5$ .............................. C07J 63/00; C07J 7/00
[52] U.S. Cl. .................................... 552/607; 568/364; 568/369
[58] Field of Search ................... 540/67, 68; 552/607, 552/569, 580, 590; 549/432, 453; 568/364, 372, 369

[56] References Cited

U.S. PATENT DOCUMENTS 3,557,158  1/1971  Lincoln et al. .................. 552/580

OTHER PUBLICATIONS

Joint Center for Chemistry, Sofia Chemical Abs., vol. 95, 1981 Abs. 43465j.
Ryakhovskaya, et al. Chem. Abs. vol. 114, 1991 Abstract 164613a.

Gadsby et al. J. Chem. Soc. C, 1968, pp. 2647–2656.

Primary Examiner—Nicholas S. Rizzo
Attorney, Agent, or Firm—Millen, White, Zelano, & Branigan

[57] ABSTRACT

A process is disclosed for the preparation of 21-bromo-4-pregnene-3,20-dione derivatives of general Formula I

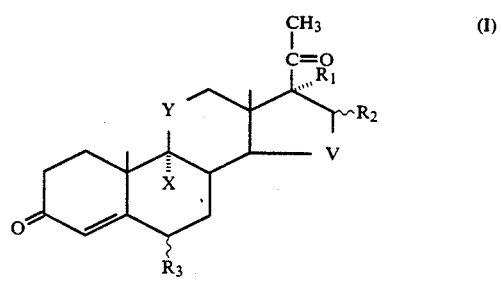

wherein
$R_1$ is a hydrogen atom, a hydroxy group or an alkanoyl group of up to 6 carbon atoms,
$R_2$ symbolizes a hydrogen atom or a methyl group, or wherein
$R_1$ and $R_2$ jointly mean an isopropylidenedioxy group, wherein
$R_3$ is a hydrogen atom, a fluorine atom or a methyl group,
V is a methylene group or ethylene group,
X is a hydrogen atom, a fluorine atom or a chlorine atom, and
Y is a methylene group, a hydroxymethylene group or a carbonyl group.

5 Claims, No Drawings

PROCESS FOR THE PREPARATION OF 21-BROMO-4-PREGNENE-3,20-DIONE DERIVATIVES

The invention relates to a process for the preparation of 21-bromo-4-pregnene-3,20-dione derivatives of general Formula I

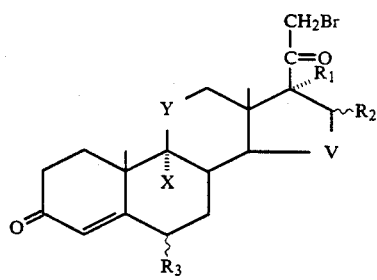

wherein
$R_1$ is a hydrogen atom, a hydroxy group or an alkanoyl group of up to 6 carbon atoms,
$R_2$ symbolizes a hydrogen atom or a methyl group, or wherein
$R_1$ and $R_2$ jointly mean an isopropylidenedioxy group, wherein
$R_3$ is a hydrogen atom, a fluorine atom or a methyl group,
V is a methylene group or ethylene group,
X is a hydrogen atom, a fluorine atom or a chlorine atom, and
Y is a methylene group, a hydroxymethylene group or a carbonyl group,
by bromination of an enamine of general Formula II

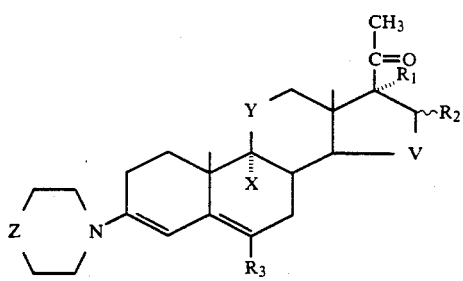

wherein
$R_1$, $R_2$, $R_3$, X, Y and V have the meanings given above and
Z is a carbon-to-carbon bond, a methylene group or an oxygen atom,
with elemental bromine in a lower alcohol of maximally 4 carbon atoms, characterized by reacting to the reaction mixture, prior to bromination, per mole of steroid 0.01 to 1 mole of methanesulfonic acid and 1 to 2 moles of an ortho ester of general Formula III $$R_4C(OR_5)_3 \quad (III)$$

wherein
$R_4$ is a hydrogen atom or an alkyl residue containing 1 to 4 carbon atoms, and
$R_5$ is an alkyl group containing 1 to 4 carbon atoms.

The 21-bromo-4-pregnene-3,20-dione derivatives of general Formula I are, as is known, valuable intermediate products usable, for example, for the preparation of 21-acyloxy-4-pregnene-3,20-dione derivatives of general Formula IV

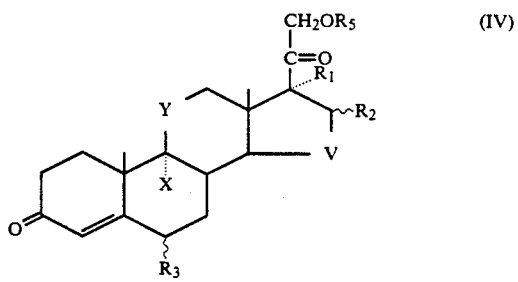

wherein
$R_1$, $R_2$, $R_3$, V, X and Y have the meanings given above and
$R_5$ is an alkanoyl group of up to 6 carbon atoms or a benzoyl group.

It is known that these 21-bromo-4-pregnene-3,20-dione derivatives can be produced by the bromination of enamines of general Formula II, the latter compounds being synthetized, in turn, from 4-pregnene-3,20-dione derivatives of general Formula V

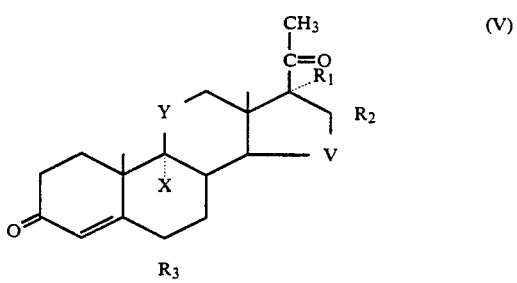

wherein $R_1$, $R_2$, $R_3$, V, X, and Y have the meanings given above.

Since the enamines of general Formula II as well as the 21-bromo-4-pregnene-3,20-dione derivatives of general Formula I produced therefrom show low stability and accordingly do not have a shelf life, the synthesis is performed under practical conditions in almost all cases by reacting these compounds further immediately after they have been formed.

Thus, Example 1 of DE-B 1,801,410 describes the conversion of 17α-hydroxy-4-pregnene-3,20-dione into 21-acetoxy-17α-hydroxy-4-pregnene-3,20-dione in a four-stage process. According to the patent, this process affords a yield of 66% of theory. However, it has been found under practical conditions that the attainable yield is, after all, substantially lower and hardly exceeds 55% of theory. Furthermore, the purity of the thus-obtained product of the process is barely 90% and accordingly unsatisfactory.

A somewhat improved process was developed by B. Gadsby et al. (John Friend and John A. Edwards, "Organic Reactions in Steroid Chemistry" vol. 2, van Nostrand Reinhold Comp., New York etc., 1972, p. 223). According to this method, as has been discovered under practical conditions, 17α-hydroxy-4-pregnene-3,20-dione is converted into 21-acetoxy-4-pregnene-3,20-dione in a yield of 62%. The purity of the resultant product is 94%. An essential deficiency of this process resides in that the bromination proper is conducted at −60° C. whereby the reaction becomes very expensive.

Additionally worth mentioning is a method described in Japanese Patent Application 81.22797 (ref. Chem. Abstr. 95 : 43465j, 1981) according to which 17α-hydroxy-4-pregnene-3,20-dione can be converted into the 21-acetoxy-17α-hydroxy-4-pregnene-3,20-dione (purity 95%) with a yield of 67% of theory, as was found under practical conditions. The disadvantage of this process resides in that the bromination is performed in the presence of perchloric acid whereby the reaction mixture becomes a great explosion hazard. Additional drawbacks of this method are that the bromination is performed in a very high dilution and takes a relatively long period of time (7-8 hours).

It is possible with the aid of the process according to this invention, as will be described in greater detail in the examples, to convert the starting compounds of general Formula V with a yield of more than 90% of theory into products of general Formula IV (purity above 93%). Additional advantages of the process of the invention can be seen in that the bromination can be performed in a relatively concentrated solution approximately at room temperature within a relatively brief period of time without the need for using materials which represent an explosion hazard.

It has been mentioned above that the enamines of general Formula II, serving as the starting compounds for the process of the present invention are, in turn, produced from the 4-pregnene-3,20-dione derivatives of general formula V. Especially suitable 4-pregnene-3,20-dione derivatives of general Formula V which can serve as preliminary products for performing the process of this invention are those containing, as the substituent $R_1$, a hydroxy group and/or, as the substituent $R_2$, a hydrogen atom or a methyl group and/or, as the substituent $R_3$, a hydrogen atom or a methyl group and/or, as the substituents X and Y, in each case hydrogen atoms and/or, as the grouping V, a methylene group.

The enamines of general Formula V are prepared conventionally, for example by heating the 4-pregnene-3,20-dione derivatives in a lower alcohol (such as methanol, ethanol, propanol or isopropanol) with piperidine, morpholine or preferably pyrrolidine to 40°-70° C. After the reaction has taken place, the enamines are crystallized from the reaction mixture after the latter has been cooled off and can be used further without any extra purification.

In order to react the enamines of general Formula II, these are suitably suspended in a lower alcohol—such as methanol, ethanol, propanol or isopropanol—the suspension is combined with about 1.0-2.0 moles of methanesulfonic acid per mole of steroid, and heated to about 40°-70° C. until a clear solution is obtained. Then, 0.01-1 mole of an ortho ester of general Formula III—preferably orthoformic acid trimethyl ester or orthoformic acid triethyl ester—is added to the solution per mole of steroid, and, within 30 to 180 minutes, at about 0° to 50° C., the stoichiometric amount of bromine is added dropwise thereto—if desired, dissolved in a lower alcohol.

After bromination has taken place, an excess of potassium carbonate—suitably dissolved in water—is added to the reaction mixture and the latter is stirred for 30-180 minutes, and the 21-bromo-4-pregnene-3,20-dione derivative of general Formula I is precipitated by pouring the mixture into ice water. The thus-obtained 21-bromo-4-pregnene-3,20-dione derivatives of general Formula I can be subsequently converted conventionally into the 21-acyloxy-4-pregnene-3,20-dione derivatives of general Formula IV by heating them under reflux in acetone or methanol with a potassium acylate—preferably potassium acetate—for 1-5 hours, and then separating the thus-formed product of the process by pouring into ice water.

The following examples serve for a more detailed description of the process of this invention.

EXAMPLE 1

(a) A suspension of 2.365 kg of 17α-hydroxy-4-pregnene-3,20-dione in 20 l of methanol is heated under agitation and a nitrogen blanket to 55° C. Then 0.946 l of pyrrolidine is added to the mixture, the latter is stirred for another hour at 55° C., cooled to −5° C., the separated 17α-hydroxy-3-(N-pyrrolidinyl)-3,5-pregnadien-20-one is suctioned off and washed with ice-cold methanol.

(b) The methanol-moist 17α-hydroxy-3-(N-pyrrolidinyl)-3,5-pregnadien-20-one is suspended at room temperature under agitation and a nitrogen blanket in 12 l of methanol, combined with 0.563 l of methanesulfonic acid, and heated until a clear solution is produced. Then the reaction mixture is allowed to cool down to room temperature, combined with 0.017 l of the trimethyl ester of orthoformic acid, and combined within 90 minutes with a solution of 1.202 kg of bromine in 5.5 l of methanol. The mixture is stirred for another 30 minutes and combined with a solution of 2.157 kg of potassium carbonate in 5.7 l of water. The mixture is stirred for another 2 hours at room temperature. Then the reaction mixture is neutralized with acetic acid, and the 21-bromo-17α-hydroxy-4-pregnene-3,20-dione is precipitated by pouring into ice water and washed with water.

(c) The still moist 21-bromo-17α-hydroxy-4-pregnene-3,20-dione is introduced under agitation and a nitrogen blanket into 24 l of acetone, combined with 1.64 kg of potassium acetate and 0.024 l of acetic acid, and heated under reflux for 210 minutes. Then 7.5 l of acetone is distilled off, the reaction mixture is allowed to cool down to room temperature, the reaction product is precipitated by pouring into ice water, washed with water, and dried under vacuum at 50° C., thus obtaining 2. 617 kg of 21-acetoxy-17α-hydroxy-4-pregnene-3,20-dione, mp 232°-335° C. Yield=94% of theory. Product purity 96.4% .

EXAMPLE 2

(a) A suspension of 40.00 g of 17α-hydroxy-16β-methyl-4-pregnene-3 11 20-trione in 90 ml of methanol is heated to 55° C. under agitation and a nitrogen blanket. Then 16 ml of pyrrolidine is added to the reaction mixture; the latter is stirred for another hour at 55° C., cooled to 0° C., the separated 17α-hydroxy-16β-methyl-3- (N-pyrrolidinyl) -3 5-pregnadiene-11, 20-dione is suctioned off and washed with ice-cold methanol.

(b) The methanol-moist 17α-hydroxy-16β-methyl-3-(N-pyrrolidinyl)-3,5-pregnadiene-11,20-dione is suspended in 590 ml of methanol at room temperature under agitation and a nitrogen blanket, combined with 8.17 ml of methanesulfonic acid, and heated until a clear solution is obtained. Then the reaction mixture is allowed to cool down to room temperature, combined with 0.67 ml of the trimethyl ester of orthoformic acid and, within 120 minutes, combined with a solution of 16.45 ml of bromine in 72.6 ml of methanol. The mixture is stirred for another 15 minutes and combined with a solution of 16.34 g of potassium carbonate in 72.6 ml of water. The mixture is stirred for another hour at room temperature. Then the reaction mixture is neutralized with acetic acid, yielding a suspension of 21-bromo-17α-hydroxy-16β-methyl-4-pregnene-3, 11, 20-trione.

(c) The suspension of 21-bromo-17α-hydroxy-16β-methyl-4-pregnene-3,11,20-trione is heated under agitation with 61.74 g of potassium acetate and for 90 minutes to 50° C. Then the methanol is extensively removed by distillation, the reaction mixture is allowed to cool down to room temperature, the reaction product is suctioned off, washed with water, and dried under vacuum at 50° C., thus obtaining 42.9 g of 21-acetoxy-17α-hydroxy-16β-methyl-4-pregnene-3,11,20-trione, mp 214°–219° C. Yield=92% of theory. Product purity 93.8%.

I claim:

1. A process for the preparation of a 21-bromo-4-pregnene-3,20-dione compound of formula I

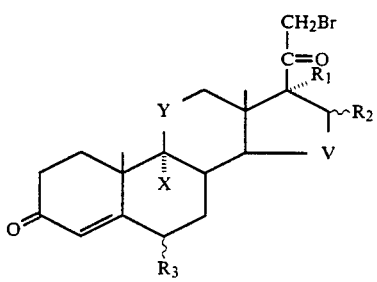

wherein
- $R_1$ is a hydrogen atom, a hydroxy group, or an alkanoyl group of up to 6 carbon atoms;
- $R_2$ is a hydrogen atom or a methyl group; or
- $R_1$ and $R_2$ jointly are an isopropylidenedioxy group;
- $R_3$ is a hydrogen atom, a fluorine atom, or a methyl group;
- V is a methylene group or ethylene group;
- X is a hydrogen atom, a fluorine atom, or a chlorine atom; and
- Y is a methylene group, a hydroxymethylene group, or a carbonyl group;

comprising brominating an enamine of formula II

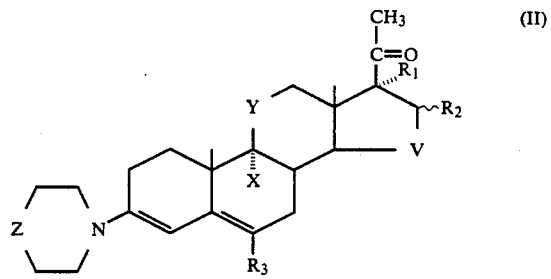

wherein $R_1$, $R_2$, $R_3$, X, Y and V have the meanings given above; and

Z is a carbon-to-carbon bond, a methylene group, or an oxygen atom;

with elemental bromine in a lower alcohol of maximally 4 carbon atoms, wherein prior to brominating the enamine, adding 1–2 moles of methanesulfonic acid per mole of the enamine and 0.01–1 moles of an ortho ester per mole of the enamine, wherein the ortho ester is of formula III $$R_4C(OR_5)_3 \quad (III)$$

wherein
- $R_4$ is a hydrogen atom or an alkyl residue of 1 to 4 carbon atoms, and
- $R_5$ is an alkyl group of 1 to 4 carbon atoms.

2. A process according to claim 2, wherein the compound of formula I is 21-bromo-17α-hydroxy-4-pregnene-3,20-dione or 21-bromo-17α-hydroxy-16β-methyl-4-pregnene-3,11,20-trione.

3. A process according to claim 2, wherein $R_1$ is a hydroxy group.

4. A process according to claim 2, wherein $R_2$ is a methyl group.

5. A process according to claim 2, wherein $R_1$ is a hydroxy group and $R_2$ is a methyl group.

* * * * *